United States Patent [19]

Shoji et al.

[11] Patent Number: 5,732,120
[45] Date of Patent: Mar. 24, 1998

[54] FLUORESCENT X-RAY ANALYZING APPARATUS

[75] Inventors: Takashi Shoji; Tadashi Utaka, both of Takatsuki; Ayako Shimazaki, Kawasaki; Kunihiro Miyazaki, Kawasaki; Tsuyoshi Matsumura, Kawasaki, all of Japan

[73] Assignees: Rigaku Industrial Corporation, Osaka; Kabushiki Kaisha Toshiba, Kanagawa, both of Japan

[21] Appl. No.: 858,892

[22] Filed: May 19, 1997

Related U.S. Application Data

[63] Continuation of Ser. No. 498,058, Jul. 5, 1995, abandoned.

[30] Foreign Application Priority Data

Jul. 6, 1994 [JP] Japan ................................ 6-179364
May 17, 1995 [JP] Japan ................................ 7-144054

[51] Int. Cl.$^6$ ............................................. G01N 23/223
[52] U.S. Cl. ........................................ 378/45; 378/210
[58] Field of Search ............................... 378/45–49

[56] References Cited

U.S. PATENT DOCUMENTS 5,148,457  9/1992  Kubota et al. ............................ 378/45
5,428,656  6/1995  Kira et al. ................................ 378/45

*Primary Examiner*—Craig E. Church
*Attorney, Agent, or Firm*—Sughrue, Mion, Zinn, Macpeak & Seas, PLLC

[57] ABSTRACT

A fluorescent X-ray analyzing apparatus includes a source of excitation (2) for irradiating a silicon-based sample (S) with primary X-rays (B2) to excite the silicon-based sample (S), a detector (4) for detecting fluorescent X-rays (B5) emitted from the silicon-based sample (S), and an analyzer (6) for analyzing elements contained in the silicon-based sample (S) based on a result of detection performed by the detector (4). The primary X-rays (B2) emitted from the source of excitation (2) have a wavelength higher than, but in the vicinity of a wavelength at an Si—K absorption edge so that generation of fluorescent X-rays (B5) of Si is suppressed to minimize a noise which would occur during detection of fluorescent X-rays (B5) of Na and Al to thereby accomplish an accurate analysis of a minute quantity of NA and Al contained in the sample (S).

7 Claims, 5 Drawing Sheets

FLUORESCENT X-RAY ANALYZING APPARATUS

This is a Continuation of application Ser. No. 08/498,058 filed Jul. 5, 1995, now abandoned.

BACKGROUND OF THE INVENTION

1. (Field of the Invention)

The present invention relates to a fluorescent X-ray analyzing apparatus for analyzing fluorescent X-rays emitted from a surface layer of a sample as a result of irradiation of primary X-rays upon the surface of the sample.

2. (Description of the Prior Art)

When impurities contained in a surface layer of a sample to be analyzed are to be detected, the existing chemical analysis takes a substantial period of time before the result of analysis is given. Therefore, it is a general practice to use fluorescent X-ray analyzing apparatuses for this purpose because with the fluorescent X-ray analyzing apparatuses it is possible to accomplish an analysis on a non-destructive basis in a relatively short period of time. Of the various fluorescent X-ray analyzing apparatuses, the fluorescent X-ray analyzing apparatus of a total reflection type is generally known to be excellent in that the signal-to-noise (S/N) ratio is high and a very small quantity of elements can be analyzed with precision. This fluorescent X-ray analyzing apparatus of the total reflection type is so designed that X-rays generated by an X-ray generator are monochromatized by a monochromator and a sample to be analyzed is irradiated with the resultant monochromatic primary X-rays incident thereupon at a minute angle of incidence, for example, 0.05 to 0.20°. Fluorescent X-rays emitted from the sample as a result of irradiation of the primary X-ray from a source of excitation including the X-ray generator and the monochromator, are then detected by a detector and elements contained in the sample are subsequently analyzed by an analyzer based on a result of detection accomplished by the detector.

Hitherto, in the case of the sample containing, as a principal component silicon (Si) such as, for example, a silicon wafer, impurities desired to be detected from the silicon-based sample are in most cases iron (Fe), nickel (Ni), titan (Ti) and copper (Cu) and, therefore, the source of excitation has long been used of a type capable of emitting the primary X-rays such as, for example, W—L$\alpha$ (tungsten-L$\alpha$) rays, W—L$\beta$ rays, Au—L$\alpha$ (gold-L$\alpha$) rays or Au—L$\beta$ rays, having a wavelength shorter than the Si—K$\alpha$ absorption edge, that is, having a relatively high energy.

However, with the remarkable advance in semiconductor technology, a high degree of purification of Si which is a basic material has come to be necessitated and, for this reason, the necessity has arisen to analyze not only the existing impurities such as Fe, Ni, etc., but also such additional impurities as natrium (Ns) and aluminum (Al).

In such case, Na and Al mixed in the Si-containing sample have their atomic number close to that of Si and, therefore, the use of the conventional source of excitation is apt to result in generation of a relatively large noise during detection of the fluorescent X-rays of Na and Al since the Si—K$\alpha$ rays are emitted in a considerable intensity in a region in the vicinity of the Al—K$\alpha$ rays and Na—K$\alpha$ rays. Because of this, the conventional apparatus has a problem in that analysis of a minute quantity of Na and Al contained in the Si-containing sample is difficult to achieve. While the fluorescent X-ray analyzing apparatus of the total reflection type utilizes, as the detector, a semiconductor detector (SSD) generally having a large solid angle, this semiconductor detector has a low resolving power with respect to the fluorescent X-ray spectrum and is susceptible to a relatively large noise during detection of the fluorescent X-rays of Na and Al if the source of excitation is used of a type capable of emitting the primary X-rays of the W—L$\alpha$ rays or the Au—L$\alpha$ rays and a relatively high intensity of the Si—K$\alpha$ rays is emitted.

SUMMARY OF THE INVENTION

In view of the foregoing, the present invention has been devised to substantially eliminate the above discussed problems and is intended to provide an improved fluorescent X-ray analyzing apparatus capable of improving the accuracy with which such elements as Na and Al mixed in the silicon-based sample can be analyzed.

In order to accomplish the foregoing object of the present invention, the present invention provides a fluorescent X-ray analyzing apparatus which comprises a source of excitation for irradiating a silicon-based sample with primary X-rays to excite the silicon-based sample, a detector for detecting fluorescent X-rays emitted from the silicon-based sample, and an analyzer for analyzing elements contained in the silicon-based sample based on a result of detection performed by the detector. The primary X-rays emitted from the X-ray generator have a wavelength higher than, but in the vicinity of a wavelength at an Si—K absorption edge.

It is to be noted that the term, "silicon-based sample", hereinabove and hereinafter used is to be understood as including not only a homogeneous material containing silicon as a principal component, but also substrate made of silicon or a silicon-containing substrate having a surface thereof deposited with a thin film of carbon, titanium or silicon nitride.

Preferably, the source of excitation includes an X-ray generator and a spectroscope for monochromatizing X-rays generated from the X-ray generator.

Preferably, a selecting means may be disposed between the source of excitation and the silicon-based sample for absorbing a wavelength component of the primary X-rays which is of a wavelength region sufficient to excite silicon, but passing therethrough a wavelength component of the primary X-rays which is of a wavelength higher than said wavelength region sufficient to excite silicon. This selecting means can be readily and easily realized by the use of at least one of a total reflection mirror and a filter.

Advantageously, the primary X-rays have a wavelength preferably greater than 6.74 angstrom and equal to or smaller than 7.7 angstrom and, more preferably, greater than 6.97 angstrom and equal to or smaller than 7.3 angstrom.

In the practice of the present invention, the primary X-rays generated from the X-ray generator may be one selected from the group consisting of one or both of W—M$\alpha$ and W—M$\beta$ rays, one or both of Ta—M$\alpha$ and Ta—M$\beta$ rays, one or both of Hf—M$\alpha$ and Hf—M$\beta$ rays, one or both of Rb—M$\alpha$ and Rb—M$\beta$ rays, Si—K$\alpha$ rays and Sr—L$\alpha$ rays. In any case, the primary X-rays are preferably projected onto the silicon-based sample at such a minute angle of incidence as to allow them to undergo a total reflection at the sample.

In a preferred embodiment, the detector has a detecting window, and the apparatus may comprise a sample chamber for accommodating the silicon-based sample, and a spectroscope chamber for accommodating the spectroscope. In this case, the detecting window of the detector is positioned within said sample chamber so as to confront the silicon-based sample, and the sample and spectroscope chambers are communicated with each other through a passage for passage of the primary X-rays therethrough. The X-ray generator may then be connected with a wall defining a the spectroscope chamber by means of a flexible connecting tube defining a passage for the primary X-rays to pass therethrough.

With the fluorescent X-ray analyzing apparatus of the present invention, the primary X-rays emitted from the source of excitation do not excite the Si—KX rays (KX representing a generic term given to the X-rays of a K—series), but do excite Na—KX rays and Al—KX rays which are of a wavelength longer than that of the Si—KX rays. Accordingly, by suppressing generation of the fluorescent X-rays of Si, a noise which would be generated during detection of the fluorescent X-rays of Na and Al can be suppressed, making it possible to accomplish analysis of a minute quantity of Na and Al.

Since the source of excitation is comprised of the X-ray generator and the monochromator for rendering the X-rays, generated by the X-ray generator, to be monochromatic, the monochromator may effectively select the primary X-rays of a wavelength longer than, but in the vicinity of the wavelength of the Si—K absorption edge before such primary X-rays are radiated towards the sample.

The disposition of the selecting means between the source of excitation and the sample is effective to allow a wavelength component of the primary X-rays which is of a wavelength region sufficient to excite silicon to be absorbed so that only a wavelength component of the primary X-rays which is of a wavelength higher than said wavelength region sufficient to excite silicon can be radiated towards the sample. Accordingly, any possible generation of the fluorescent X-rays of Si from the sample can further be suppressed.

Furthermore, in practice of the present invention, both of the sample chamber and the spectroscope chamber are evacuated to a low pressure and, therefore, any possible attenuation of the primary X-rays to be radiated upon the sample can advantageously be avoided.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE PREFERRED EMBODIMENTS

Some preferred embodiments of the present invention will now be described with reference to the accompanying drawings.

Figure 1:
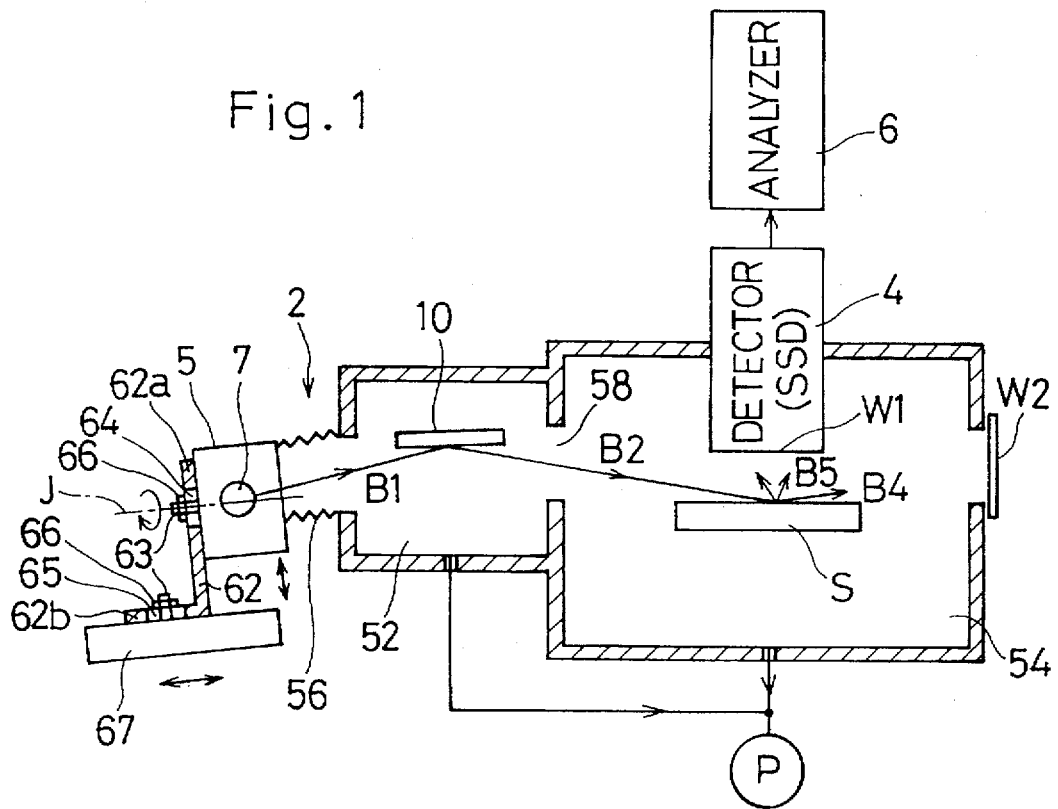
FIG. 1 is a schematic side sectional view showing a fluorescent X-ray analyzing apparatus according to a first preferred embodiment of the present invention.

Referring first to FIG. 1, there is shown a schematic side sectional view of a fluorescent X-ray analyzing apparatus of a total reflection type according to a first preferred embodiment of the present invention. This fluorescent X-ray analyzing apparatus of the total reflection type shown therein comprises a source of excitation 2 comprising an X-ray generator 5 and a monochromator 10 formed by an analyzing crystal or an artificial multilayered grating, a detector 4 such as, for example, a semiconductor detector (SSD) and an analyzer 6 such as, for example, a multiple wave height analyzer. This apparatus is so designed that X-rays B1 generated from the X-ray generator 5 are monochromatized by the monochromator 10 and the resultant monochromatic primary X-rays B2 are projected onto a sample S of a kind containing, as a principle component, Si (silicon) such as a silicon wafer so as to be incident thereupon at a minute angle of incidence, for example, 0.05° to 0.20°. The sample S when irradiated with the primary X-rays B2 from the source of excitation 2 emits fluorescent X-rays B5 which are detected by the detector 4 and, based on a result of detection by the detector 4, the analyzer 6 analyzes elements contained in the sample S. Various component parts of the apparatus will now be described in details.

The source of excitation 2 includes the X-ray generator 5 for generating the X-rays B1 and the monochromator 10 for monochromatizing the X-rays B1. This source of excitation 2 is so operable as to irradiate the sample S with the monochromatic primary X-rays B2 to excite the latter. The monochromator 10 is accommodated within a monochromator chamber 52. The sample S is accommodated within a sample chamber 54 of a structure having a sample access window W2 through which the sample S can be placed inside and removed from the sample chamber 54, and the detector 4 has a detecting window W1 positioned within the sample chamber 54 so as to confront the sample S. The sample chamber 54 and the monochromator chamber 52 are communicated with each other through a passage 58 defined in a partition wall for passage of the primary X-rays B2 therethrough. To secure a minute angle of incidence at which the primary X-rays B2 impinge upon the sample S within the sample chamber 54, the source of excitation 2 is of a structure which will now be described.

The X-ray generator 5 includes an X-ray source 7 of a rotary target mounted on a generally L-shaped support member 62 which is in turn fixedly mounted on a base support 67. The L-shaped support member 62 has a vertical arm 62a formed with a slot 64 through which a bolt 63 secured to the X-ray generator 5 extends with a nut 66 externally threaded thereto. The X-ray generator 5 so supported by the L-shaped support member 62 is adjustably movable along the slot 64 in a direction parallel to the lengthwise direction of the slot 64 and is also adjustably rotatable about the longitudinal axis J of the bolt 63. The L-shaped support member 62 also has a horizontal arm 62b perpendicular to the vertical arm 62a, which arm 62b is also formed with a slot 65 through which a bolt 63 secured to the base support 67 extends with a nut 66 externally threaded thereto so that the L-shaped support member 62 and, hence, the X-ray generator 5 carried by the vertical arm 62a thereof, can be adjustably moved in a direction parallel to the lengthwise direction of the slot 65. It is to be noted that the slot 65 in the horizontal arm 62b of the L-shaped support member 62 has its longitudinal axis oriented perpendicular to that of the slot 64 in the vertical arm 62a thereof. Thus, it will be understood that the X-ray generator 5 can be adjusted in position in a direction up and down, front and aft and about the longitudinal axis of each bolt 63.

The X-ray generator 5 supported in the manner described above is coupled with the monochromator chamber 52 through an axially foldable and flexible connecting tube 56 such as, for example, a connecting bellows, made of stainless steel or rubber material secured at one end to a wall defining the monochromator chamber 52. Adjustment in position of the X-ray generator 5 results in a corresponding movement of the axially foldable and flexible connecting tube 56 such that the Bragg's angle θ satisfying a diffraction condition of the monochromator 10 and the angle of incidence of the primary X-rays B2 incident upon the sample S can be adjusted finely.

Figure 3:
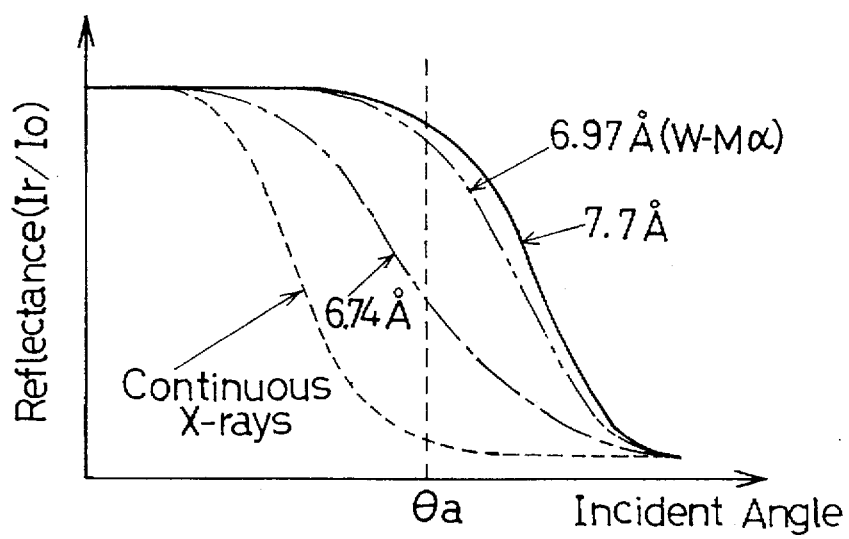
FIG. 3 is a characteristic graph showing the reflectance of a reflecting mirror used in the fluorescent X-ray analyzing apparatus according to the second preferred embodiment of the present invention.

The source of excitation 2 employed in the practice of the present invention emits the primary X-rays B2 required to detect the presence of impurities, Na and Al, mixed in the sample S and is, for this purpose, capable of a wavelength greater than the wavelength, 6.74 angstrom, of the Si—K absorption edge and approximating to the Si—K absorption edge, for example, a wavelength greater than 6.74 angstrom and equal to or smaller than 7.7 angstrom. The reason for selection of the wavelength greater than the wavelength, 6.74 angstrom, of the Si—K absorption edge is for the purpose of suppressing excitation of Si contained in the sample S as minimal as possible. If Si is otherwise excited, a relatively large noise is produced as shown in FIG. 3, causing the detector 4 to fail to detect the fluorescent X-rays B5 attributable to the presence of Na and Al with high accuracy. The reason for selection of 7.7 angstrom for the uppermost limit of the wavelength of the primary X-rays B2 emitted by the source of excitation 2 is that, in order to avoid the possibility that a component of the primary X-rays B2 which has been reflected from the sample S constitutes a noise when entering the detector 4, the primary X-rays B2 must be of a wavelength separate a substantial quantity from both the wavelength (8.34 angstrom) of the Al—Kα rays and the wavelength (11.9 angstrom) of the Na—Kα rays.

Preferably, the primary X-rays B2 emitted by the source of excitation 2 has a wavelength ranging from the lowermost limit greater than 6.97 angstrom, which is the wavelength of the W—Mα rays, to the uppermost limit not greater than 7.3 angstrom, which is the wavelength of the Rb—Lα rays, more preferably not greater than 7.13 angstrom which is the wavelength of Si—Kα rays. As will be described later, it has been found that Rb or Si other than W as a target material for the X-ray source 7 and the Rb—Lα rays or the Si—Kα rays for the primary X-rays B2 emitted from the X-ray source 7 are conveniently employed in the practice of the present invention and, as shown in FIG. 3, the wavelengths of the Rb—Lα rays and the Si—Kα rays are 7.3 and 7.13 angstrom, respectively.

In the source of excitation 2 of the type discussed above, W may be employed as a target material for the X-ray source 7 and the W—Mα rays or W—Mβ rays may be employed as the primary X-rays B2 for analysis of Na and Al. Also, it is possible to employ, for the primary X-rays B2, primary X-rays of a kind containing both of the W—Mα and W—Mβ rays while a monochromator of a low resolution of diffraction is used. Again, one or both of the Ta—Mα (tantalum-Mα) rays and the Ta—Mβ rays, one or both of the Hf—Mα (hafnium-Mα) rays and the Hf—Mβ rays or one or both of the Rb—Mα (rubidium-Mα) rays and the Rb—Mβ rays may also be used in the practice of the present invention. Furthermore, the Si—Kα rays or the Sr—Lα (strontium-Lα) rays may be employed as well.

In the fluorescent X-ray analyzing apparatus of the present invention, both the sample chamber 54 and the monochromator chamber 52 are evacuated by a vacuum pump P to a low pressure of about 0.1 Torr. Therefore, absorption of the X-rays by the air contained in the monochromator chamber 52 which has hitherto been equalized to the atmospheric pressure can be advantageously avoided to minimize attenuation of the X rays B1 and B2. It is to be noted that the interior of the X-ray generator 5 is also evacuated to about $10^{-6}$ Torr.

In the prior art fluorescent X-ray analyzing apparatus, since the sample chamber 54 is evacuated to a low pressure and the monochromator chamber 52 is equalized to the atmospheric pressure, the passage 58 between the monochromator chamber 52 and the sample chamber 54 has been provided with a beryllium window plate. However, in the fluorescent X-ray analyzing apparatus according to the illustrated embodiment of the present invention, the chambers 52 and 54 are of an equal pressure, eliminating the need to use the beryllium window plate and, therefore, the primary X-rays B2 passing through the passage 58 will not attenuate. In addition, while in the prior art apparatus an window plate of 12 μm in thickness made of beryllium has also been used at the detection window W1 of the detector (SSD), the detection window W1 of the detector 4 employed in the apparatus of the illustrated embodiment makes use of a window plate of a thickness not greater than 1 μm, for example, 0.6 μm, made of polyester is employed and, therefore, any possible attenuation of the fluorescent X-rays B5 entering the detection window W1 is avoided advantageously.

When the primary X-rays B2 emitted from the X-ray source 7 impinge upon the sample S, a part of the primary X-rays B2 undergoes a total reflection to produce reflected rays B4 and the remaining portion thereof excites Na and Al mixed in a surface or a region adjacent the surface of the sample S. The detector (SSD) 4 is operable to detect the fluorescent X-rays B5 peculiar to and emitted from Na and Al as a result of excitation. The reflected rays B4 are reflected at a minute angle of reflection substantially equal to the angle of incidence of the primary X-rays B2 upon the sample S, carrying scattered X-rays away from the sample S. Consequently, the reflected rays B4 and the scattered X-ray which constitute a cause of the noise do hardly enter the detector 4 and, therefore, the noise component is low as compared with an output level of the fluorescent X-rays B5 detected by the detector 4, that is, a high S/N ratio can be obtained. Based on the result of detection of the intensity of the fluorescent X-rays detected by the detector 4, the analyzer 6 analyzes elements contained in the sample S to give an X-ray spectrum of interest.

Thus, the fluorescent X-ray analyzing apparatus of the present invention is effective to accomplish analysis of a minute quantity of Na and Al by suppressing generation of fluorescent X-rays attributable to Si to thereby minimize the noise during detection of the Na—KX rays and the Al—KX rays.

Figure 2:
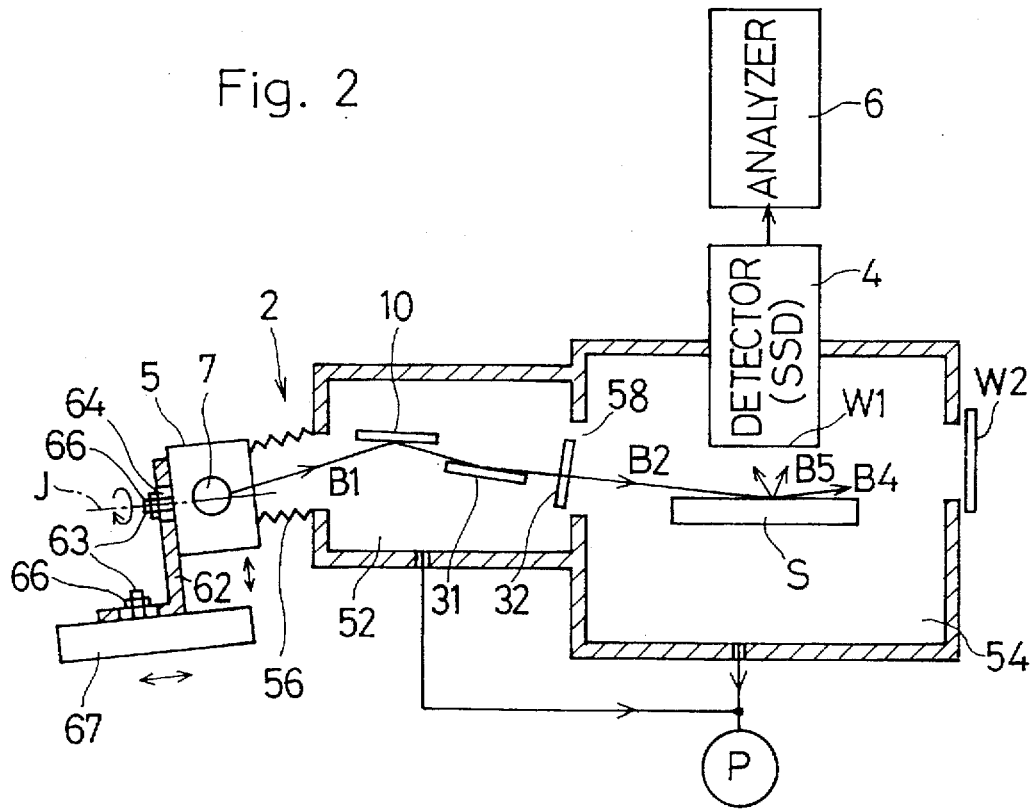
FIG. 2 is a schematic side sectional view showing the fluorescent X-ray analyzing apparatus according to a second preferred embodiment of the present invention.

In the foregoing description, the primary X-rays radiated to the sample S have been described as having a wavelength greater than the wavelength of 6.74 angstrom which is the absorption edge of Si. However, where the resolution of diffraction of the monochromator 10 is low, a component smaller than the wavelength of the above described absorption edge or a component having greater energy than the absorption edge may remain to such an extent as to result in excitation of Si contained in the sample S. The fluorescent X-ray analyzing apparatus according to a second preferred embodiment of the present invention shown in FIG. 2 is so designed as to eliminate this problem. Referring now to FIG. 2, a total reflection mirror 31 in the form of a Si plate and a filter in the form of a Si film are disposed between the monochromator 10 and the sample S. Both the total reflection mirror 31 and the filter 32 are accommodated within the monochromator chamber 52 together with the monochromator 10. Other structural features of the fluorescent X-ray analyzing apparatus shown in FIG. 2 are identical with those shown in FIG. 1 and, therefore, the details thereof are not reiterated for the sake of brevity.

The reflectance of the total reflection mirror 31, that is, the intensity Ir of the reflected X-rays relative to the intensity Io of the incident X-rays, is such as shown in FIG. 3 and the total reflection mirror 31 exhibits, in the vicinity of a critical angle θa, an extremely low reflectance for continuous X-rays (of a wavelength within the range of 3.5 to 5.0 angstrom) and a considerably low reflectance for X-rays of a wavelength substantially equal to 6.74 angstrom which is the wavelength at the absorption edge of Si. In contrast thereto, the total reflection mirror 31 exhibits an extremely high reflectance in the vicinity of the critical angle θa for the W—Mα rays of 6.97 angstrom in wavelength and X-rays of a wavelength greater than that of the W—Mα rays, for example, X-rays of 7.7 angstrom in wavelength. Accordingly, if the angle of incidence of the primary X-rays B2 upon the total reflection mirror 31 is chosen to match with the critical angle θa, the X-rays of a wavelength equal to or smaller than 6.74 angstrom can be cut off and the X-rays of a wavelength greater than 6.74 angstrom can be reflected and, therefore, any possible excitation of Si at the sample S can be advantageously suppressed.

Figure 4:
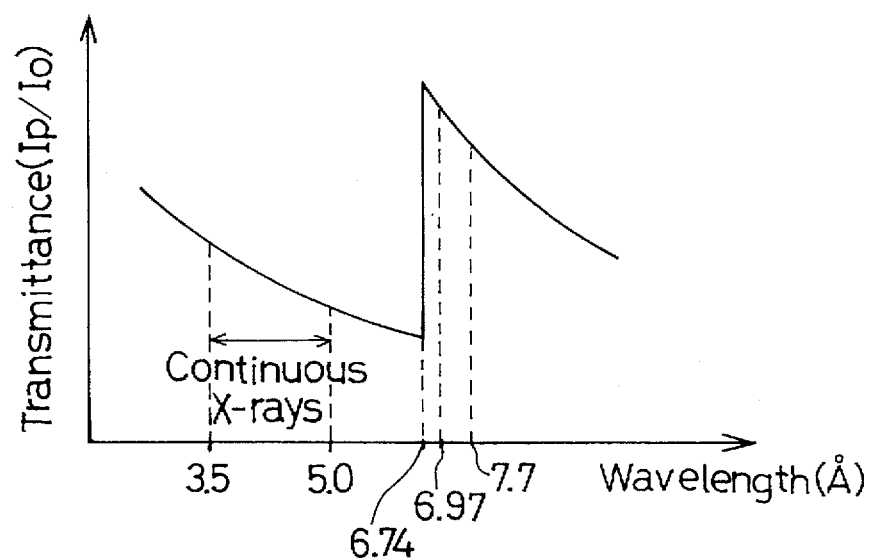
FIG. 4 is a characteristic graph showing the transmittance of a filter used in the fluorescent X-ray analyzing apparatus according to the second preferred embodiment of the present invention.

The transmittance of the filter 32, that is, the intensity Ip of the X-rays transmitted therethrough relative to the intensity Io of the incident X-rays, is such as shown in FIG. 4 and the filter 32 exhibits a low transmittance for the continuous X-rays and the X-rays having a wavelength substantially equal to 6.74 angstrom which is the wavelength at the absorption edge of Si, but an extremely high transmittance for the W—Mα rays of 6.97 angstrom in wavelength and the X-rays of a wavelength greater than that of the W—Mα rays, for example, X-rays of 7.7 angstrom in wavelength. Accordingly, the excitation of Si at the sample S can also be advantageously suppressed.

According to the second preferred embodiment of the present invention shown in FIG. 2, a wavelength component of the primary X-rays B2 rendered to be monochromatic by the monochromator 10 which is smaller than 6.74 angstrom which is the wavelength at the absorption edge of Si is cut off by the total reflection mirror 31 and the filter 32, and therefore, even though the sample S is irradiated with these primary X-rays B2, excitation of Si at the sample S is advantageously suppressed. On the other hand, the X-rays of a wavelength greater than 6.74 angstrom, that is, the X-rays participating in excitation of Na and Al of interest upon irradiation of the sample S pass through the total reflection mirror 31 and the filter 32, and therefore, the intensity of the fluorescent X-rays attributable to Na and Al of interest desired to be detected by the detector 4 will not be lowered.

Also, while the total reflection mirror 31 has a feature in that the X-rays of a wavelength extremely smaller than 6.74 angstrom which is the wavelength at the absorption edge of Si, for example, the continuous X-rays and the X-rays of a wavelength smaller than the wavelength thereof, are positively cut off (exhibiting a low reflectance), it has a problem in that the extent to which the X-rays of a wavelength slightly smaller than 6.74 angstrom are cut off is low (exhibiting a high reflectance). In contrast thereto, the filter 32 has a problem in that the extent to which the continuous X-rays and the X-rays of a wavelength smaller than the wavelength thereof is somewhat low (exhibiting a high transmittance), it has a feature in that the extent to which the X-rays of a wavelength slightly smaller than 6.74 angstrom is high (exhibiting a low transmittance). Accordingly, the use of the total reflection mirror 31 in combination with the filter 32 is effective to assuredly cut off the continuous X-rays and the X-rays of a wavelength smaller than the wavelength thereof and also to assuredly cut off the X-rays slightly lower than 6.74 angstrom and, accordingly, excitation of Si in the sample S can effectively be suppressed to allow the analysis of Na and Al to be accomplished with high accuracy.

It is to be noted that, in the practice of the second preferred embodiment of the present invention, one of the total reflection mirror 31 and the filter 32 may be dispensed with, and even the use of one of them may bring about similar effects.

Figure 5A:
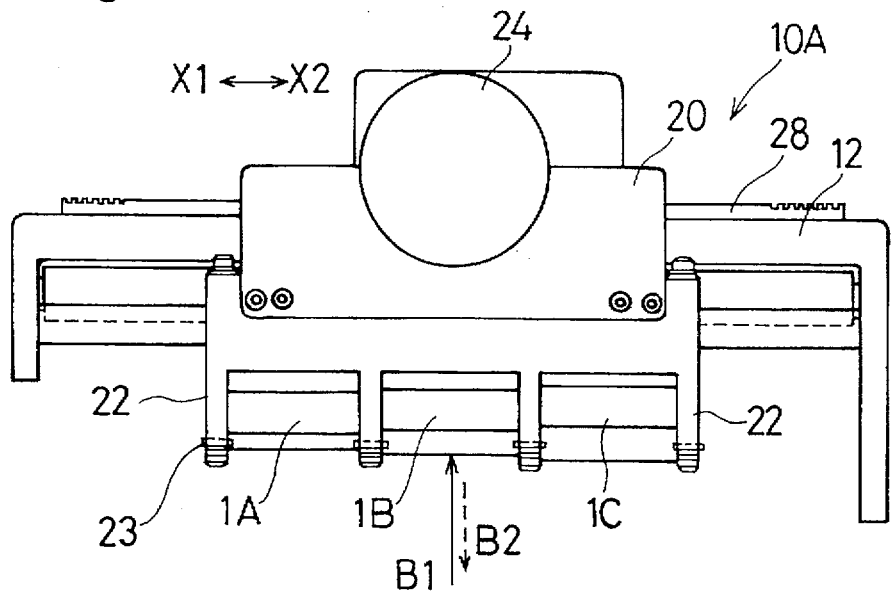
FIG. 5A is a schematic front elevational view showing a modified form of an analyzer.
Figure 5B:
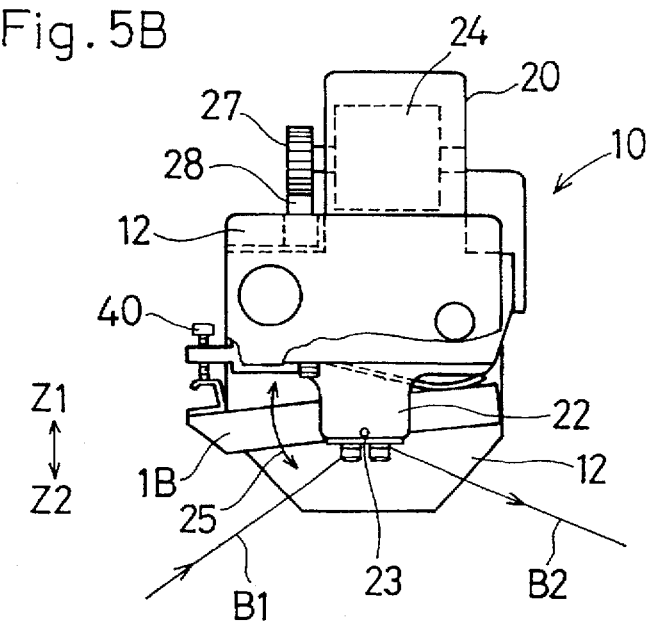
FIG. 5B is a schematic side view of the analyzer shown in FIG. 5A.
Figure 6:
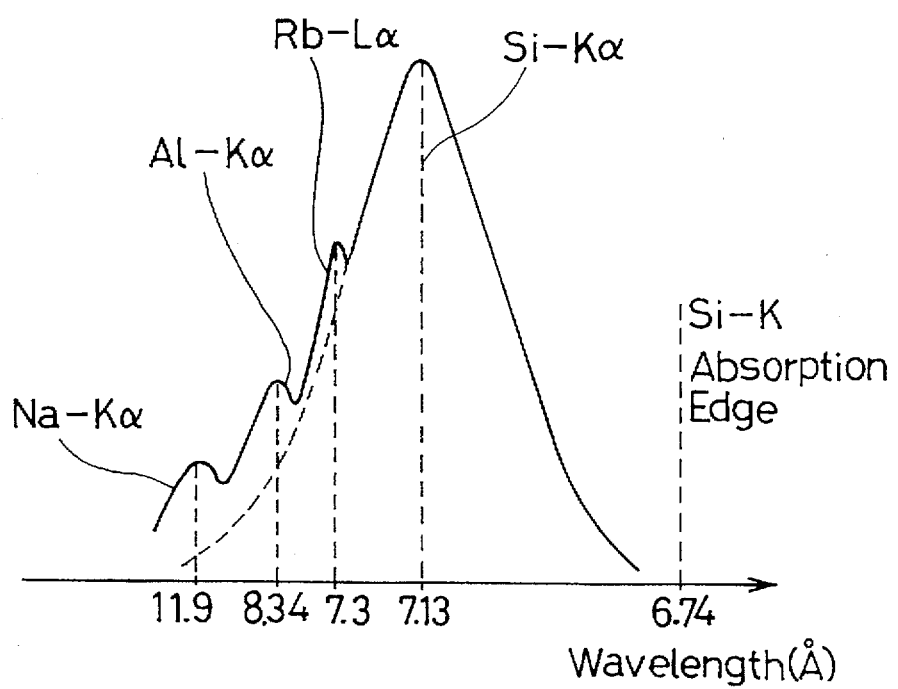
FIG. 6 is a characteristic graph showing the X-ray spectrum.

FIG. 5A shows a schematic front elevational view of a modified form of the monochromator and FIG. 5B shows a schematic side view of such modified monochromator. The modified monochromator now identified by 10A can be utilized in place of the monochromator 10 shown in FIG. 1 and used in the first preferred embodiment of the present invention or the monochromator 10 shown in FIG. 2 and used in the second preferred embodiment of the present invention, not only for quick and ready analysis of such light elements as Na and Al, but also for quick and ready analysis of heavy elements such as Fe and Ni. In other words, by preparing a plurality of monochromator elements such as artificial multi-layered gratings operable to diffract the primary X-rays B2 and selectively utilizing one of the monochromator elements according to the type of an element to be detected, a plurality of elements can be detected from one and the same sample without moving the sample. By way of example, the monochromator 10A shown in FIGS. 5A and 5B can selectively utilize a monochromator element 1A when the W—Mα rays or the W—Mβ rays are desired to be diffracted for analysis of Na and Al or monochromator elements 1B and 1C when W—Lα rays and the W—Lβ rays are desired to be diffracted for analysis of Fe and Ni, respectively.

Referring to FIG. 5A, the monochromator 10A is provided with a fixed frame 12 and a movable carriage 20. The movable carriage 20 includes a plurality of grating supports 22, each neighboring grating supports 22 accommodating a corresponding monochromator element 1A, 1B or 1C therebetween. Since the monochromator elements 1A to 1C have respective support pins 23 fixed thereto and rotatably supported by the grating supports 22, the monochromator elements 1A to 1C are rotatably fitted to the movable carriage 20. This movable carriage 20 is driven on and along a rack 28 by a drive motor 24 used to drive a pinion 27 meshed with the rack 28 so that the movable carriage 20 can move on the frame 12 in an X1–X2 direction (horizontal direction). As best shown in FIG. 5B, the movable carriage 20 has an adjustment screw 40 movable in a Z1–Z2 direction (vertical direction) for adjusting the angle of each of the monochromator elements 1A to 1C around the support pins 23 as indicated by the arrow 25.

If for the primary X-rays B2 for analysis of Na and Al discussed hereinabove, the Ta—Mα rays, Ta—Mβ rays, Hf—Mα rays, Hf—Mβ rays, the Rb—Mα rays or Rb—Mβ rays other than the W—Mα and the W—Mβ rays are employed, switching of one of the monochromator elements makes it possible to use one of the following rays for the primary X-rays B2 for analysis of Fe and Ni:

| For Analysis of Na and Al | For Analysis of Fe and Ni |
| --- | --- |
| Ta-Mα Rays, Ta-Mβ Rays | Ta-Lα Rays, Ta-Lβ Rays |
| Hf-Mα Rays, Hf-Mβ Rays | Hf-Lα Rays, Hf-Lβ Rays |
| Rb-Mα Rays, Rb-Mβ Rays | Rb-Kα Rays, Rb-Kβ Rays |
| Sr-Lα Rays | Sr-Kα Rays |

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, although in describing the preferred embodiments of the present invention the fluorescent X-ray analyzing apparatus has been referred to as a total reflection type, it may not be always of the total reflection type.

Accordingly, such changes and modifications are, unless they depart from the scope of the present invention as delivered from the claims annexed hereto, to be construed as included therein.

What is claimed is:

1. A fluorescent X-ray analyzing apparatus which comprises:

a source of excitation for irradiating a silicon-based sample with primary X-rays to excite the silicon-based sample, said source of excitation including an X-ray generator and a monochromator for monochromatizing X-rays generated from the X-ray generator so as to have a wavelength greater than, but in the vicinity of a wavelength at an Si—K absorption edge, within the region of wavelength greater than 6.74 angstrom and equal to or smaller than 7.7 angstrom;

a detector for detecting fluorescent X-rays emitted from the silicon-based sample; and an analyzer for analyzing elements contained in the silicon-based sample based on a result of detection performed by the detector, wherein the fluorescent X-rays to be detected have wavelengths not smaller than 8.34 angstrom and not greater than 11.9 angstrom.

2. The fluorescent X-ray analyzing apparatus as claimed in claim 1, wherein said detector has a detecting window, and further comprising a sample chamber for accommodating the silicon-based sample, said detecting window of the detector being positioned within said sample chamber so as to confront the silicon-based sample, and a monochromator chamber for accommodating the monochromator, said sample and monochromator chambers being communicated with each other through a passage for passing the primary X-rays therethrough, said X-ray generator being connected with a wall defining the monochromator chamber by means of a flexible connecting tube defining a passage for the primary X-rays to pass therethrough.

3. The fluorescent X-ray analyzing apparatus as claimed in claim 1, further comprising a selecting means disposed between the source of excitation and the silicon-based sample, said selecting means being operable to absorb a wavelength component of the primary X-rays which is of a wavelength region sufficient to excite silicon, but pass therethrough a wavelength component of the primary X-rays which is of a wavelength greater than said wavelength region sufficient to excite silicon.

4. The fluorescent X-ray analyzing apparatus as claimed in claim 3, wherein said selecting means includes at least one of a total reflection mirror and a filter.

5. The fluorescent X-ray analyzing apparatus as claimed in claim 1, wherein said primary X-rays are projected onto the silicon-based sample at such a minute angle of incidence as to allow them to undergo a total reflection at the sample.

6. The fluorescent X-ray analyzing apparatus as claimed in claim 1, wherein said primary X-rays have a wavelength greater than 6.97 angstrom and equal to or smaller than 7.3 angstrom.

7. The fluorescent X-ray analyzing apparatus as claimed in claim 1, wherein said primary X-rays are selected from the group consisting of one or both of W—Mα and W—Mβ rays, one or both of Ta—Mα and Ta—Mβ rays, one or both of Hf—Mα and Hf—Mβ rays, one or both of Rb—Mα and Rb—Mβ rays, Si—Kα rays and Sr—Lα rays.

* * * * *